(12) United States Patent
Sarvazyan (10) Patent No.: US 8,649,876 B2
(45) Date of Patent: *Feb. 11, 2014

(54) LEADLESS SYSTEM FOR DEEP BRAIN STIMULATION USING TIME REVERSAL ACOUSTICS

(71) Applicant: Armen P. Sarvazyan, Lambertville, NJ (US)

(72) Inventor: Armen P. Sarvazyan, Lambertville, NJ (US)

(73) Assignee: Artann Laboratories Inc., Trenton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/740,622

(22) Filed: Jan. 14, 2013

(65) Prior Publication Data

US 2013/0131754 A1    May 23, 2013

Related U.S. Application Data

(63) Continuation-in-part of application No. 13/448,530, filed on Apr. 17, 2012, which is a continuation-in-part of application No. 13/028,301, filed on Feb. 16, 2011, which is a continuation-in-part of application No. 12/766,383, filed on Apr. 23, 2010, now Pat. No. 7,985,184, which is a continuation-in-part of application No. 11/223,259, filed on Sep. 10, 2005, now Pat. No. 7,713,200.

(51) Int. Cl.
*A61N 1/36* (2006.01)
*A61N 1/372* (2006.01)

(52) U.S. Cl.
CPC ........ *A61N 1/37217* (2013.01); *A61N 1/37252* (2013.01)
USPC ........................................... 607/60

(58) Field of Classification Search
USPC .......................................... 607/2, 32, 60, 437
See application file for complete search history.

(56) References Cited

U.S. PATENT DOCUMENTS

| | | |
|---|---|---|
| 5,092,336 A | 3/1992 | Fink |
| 5,405,367 A | 4/1995 | Schulman et al. |
| 5,716,377 A | 2/1998 | Rise |
| 5,782,798 A | 7/1998 | Rise |
| 6,016,449 A | 1/2000 | Fischell |
| 6,037,704 A | 3/2000 | Welle |
| 6,366,816 B1 | 4/2002 | Marchesi |

(Continued)

FOREIGN PATENT DOCUMENTS

DE    4330680 A1    3/1995

*Primary Examiner* — Christopher D Koharski
*Assistant Examiner* — Jeremiah Kimball
(74) *Attorney, Agent, or Firm* — Boris Leschinsky (57) ABSTRACT

A leadless Deep Brain Stimulation system includes an implantable stimulator configured to convert incoming acoustic energy into an electric stimulation signal. The acoustic energy is provided by one or more external transmitters acoustically coupled to a head of the subject. To focus ultrasound energy onto the location of the stimulator, a wireless beacon (including a piezoelectric receiving transducer and an RF emitting antenna) is incorporated with the stimulator for providing an electromagnetic feedback signal to the external controller. The external controller is configured to send an initial unfocused acoustic signal towards the stimulator and receive the electromagnetic radiofrequency feedback signal generated by the receiving piezotransducer when affected by the acoustic signal after reverberation in the skull. This signal is then time-reversed and used to send a second signal towards the stimulator. This signal is inherently focused on the site of the stimulator and is configured to carry sufficient energy to operate the stimulator for DBS purposes.

18 Claims, 6 Drawing Sheets

(56) References Cited

U.S. PATENT DOCUMENTS

| | | |
|---|---|---|
| 6,427,086 B1 | 7/2002 | Fischell |
| 6,490,469 B2 * | 12/2002 | Candy .......................... 600/407 |
| 7,010,351 B2 | 3/2006 | Firlik |
| 7,013,177 B1 | 3/2006 | Whitehurst |
| 7,489,967 B2 * | 2/2009 | Von Arx et al. ................ 607/32 |
| 7,713,200 B1 * | 5/2010 | Sarvazyan et al. ............ 600/437 |
| 7,894,904 B2 | 2/2011 | Cowan |
| 2003/0005770 A1 * | 1/2003 | Berryman ....................... 73/602 |
| 2004/0162507 A1 * | 8/2004 | Govari ............................. 601/2 |
| 2004/0162550 A1 * | 8/2004 | Govari et al. .................. 606/27 |
| 2004/0172083 A1 * | 9/2004 | Penner ............................ 607/35 |
| 2010/0228308 A1 * | 9/2010 | Cowan et al. .................. 607/14 |

* cited by examiner

LEADLESS SYSTEM FOR DEEP BRAIN STIMULATION USING TIME REVERSAL ACOUSTICS

CROSS-REFERENCE DATA

This patent application is a continuation-in-part of a co-pending U.S. patent application Ser. No. 13/448,530 filed 17 Apr. 2012 entitled "SYSTEMS FOR REMOTE GENERATION OF ELECTRICAL SIGNAL IN TISSUE BASED ON TIME-REVERSAL ACOUSTICS"; which in turn is a continuation-in-part of a co-pending U.S. patent application Ser. No. 13/028,301 filed 16 Feb. 2011 entitled "ULTRASOUND DIAGNOSTIC AND THERAPEUTIC DEVICES"; which is in turn a continuation-in-part of a U.S. patent application Ser. No. 12/766,383 filed 23 Apr. 2010 entitled "Ultrasound-assisted drug-delivery method and system based on time reversal acoustics", now U.S. Pat. No. 7,985,184; which in turn is a continuation-in-part of U.S. patent application Ser. No. 11/223,259 filed 10 Sep. 2005 entitled "Wireless beacon for time-reversal acoustics, method of use and instrument containing thereof", now U.S. Pat. No. 7,713,200. All of the above mentioned patent documents are incorporated herein by reference in their respective entireties.

BACKGROUND OF THE INVENTION

The present invention relates generally to neurostimulators. More particularly, the invention describes a leadless ultrasound-based system configured for electrical stimulation of the brain.

Deep brain stimulation (DBS) is one of the most important therapies in modern functional neurosurgery. First approved by the FDA in 1997, deep brain stimulation inactivates, but does not destroy, the parts of the brain responsible for example for the movement disorders. Due to its safety profile and efficacy, DBS evolved from a last-resort therapeutic option to a modality that is now routinely offered to patients and has been used to treat various neurological disorders.

DBS of the thalamus is primarily used to treat disabling tremor, especially tremor that affects one side of the body substantially more than the other. Studies have shown that DBS may significantly reduce tremor in about two thirds of patients with Parkinson's disease (PD). Tremor may not be eliminated, and may continue to cause some impairment. DBS of the globus pallidus is useful in treatment of dyskinesias as well as tremor, and may improve other symptoms, as well. DBS of the subthalamic nucleus may have an effect on most of the main motor features of PD, including bradykinesia, tremor, and rigidity.

Treatment sites for movement disorders may be identified by probing brain tissue and a site predetermined for treatment is selected. As noted for movement disorders, known regions of the brain suitable for neurostimulation include, but are not limited to, the ventral intermediate thalamus, subthalamic nucleus, and internal globus pallidus.

Similarly, DBS has been pursued as a treatment for pain for the past 30 years. Peripheral pain signals are transmitted via the spinothalamic tract of the spinal cord and synapse primarily in the thalamus. Thus, the area where they synapse was seen as a prime target for DBS and was the focus of much of the early research. DBS continues to be pursued as a therapy in chronic pain patients. Today, the pain indications that either exist or seem most promising for potential treatment by deep brain stimulation include: neuropathic pain; Complex Regional Pain Syndrome (CRPS), Type II; steady, burning pain; lancinating, shooting pain; tactile hypersensitivity; or partial or complete sensory loss. The targets for DBS for pain typically include the following sites:

Neuropathic Pain: Medial Lemniscus, Ventrobasal (VB) area of the thalamus, including the ventral posteromedial (VPM) and the ventral posterolateral (VPL) nuclei, Internal Capsule, Motor Cortex, Cingulate gyrus (also known as cingulate cortex), Posterior complex of the thalamus (PO), Ventrolateral nucleus of the thalamus (VL).

Nociceptive Pain: Periventricular grey (PVG) matter and periaqueductal grey (PAG) matter, which are sometimes simply called periventricular grey and periaqueductal grey.

Similar targets in the brain are emerging for other DBS applications. Published targets for the treatment of depression would include, but are not limited to, one or more of the cerebellar vermis, the anterior cingulate gyrus, the dorsal prefrontal cortex, the dorsal raphe nuclei, the median raphe nuclei, and the locus coeruleus. Published targets for the treatment of epilepsy, obesity, and diabetes would include, but are not limited to, the nucleus of tractus solitarius (NTS), the sub thalamic nucleus, the hippocampus, the medial thalamus and the temporal lobe.

Upper regions of the brain, e.g., the cortex, that have been affected by stroke or injury also benefit from stimulation treatments and have been shown to be effective in rehabilitating motor performance of distal extremities. In this stroke rehabilitation treatment the electrode is placed on the dura, the membrane that covers the brain, and used to deliver stimulation to the cortex.

In addition to its established role for the treatment of movement disorders, promising results have now been reported in epilepsy and psychiatric diseases. New applications of DBS are currently being proposed for diseases previously considered out of the realm of neurosurgical therapies. DBS has now been suggested as an emergent treatment for various conditions, including depression, hypertension, Alzheimer's disease, Parkinson's disease, Tourette syndrome, obsessive compulsive disorder, minimally conscious states, memory improvement, aggressiveness, and even drug addiction and obesity. In recent years, in addition to its therapeutic effects, the use of DBS systems as part of brain-machine interfaces has been extensively discussed.

Figure 1:
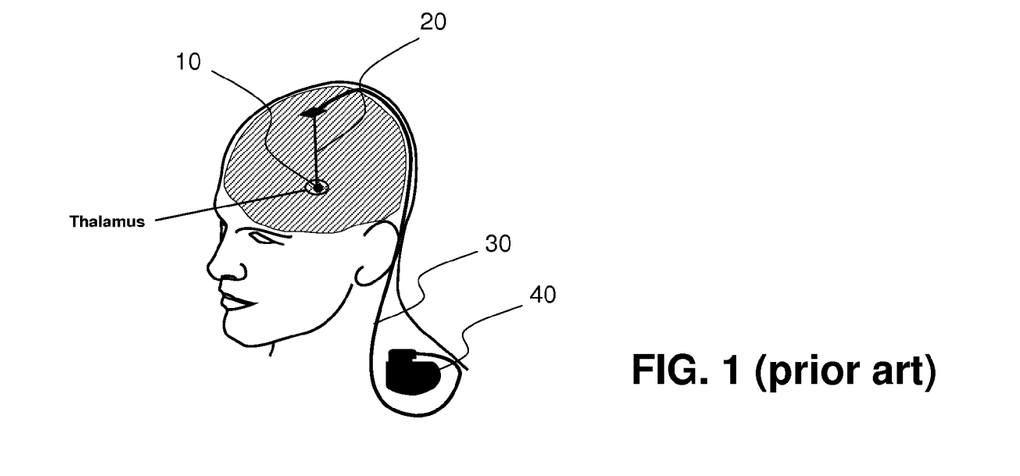
FIG. 1 is a general outline of the prior art DBS system with direct attachment of electrical leads to the implantable neurostimulator.

FIG. 1 illustrates conventional realization of DBS. Current DBS systems include one or more intracranial DBS electrodes 10 implanted into the subject's brain (typically in a thalamus section), optional adaptors to fix the electrodes in place, an implantable stimulator 40 such as an implantable pulse generator (IPG), and a lead 20 with an extension cable 30 to connect the DBS electrode 10 to the stimulator 40. About two weeks after implanting the electrode 10 and a lead 20, a separate surgery is performed to implant one or two neurostimulators 40 under the collarbone. Wires of the extension cable 30 are at the same time placed under the skin, which run behind the ears and down the neck, to connect the neurostimulators 40 with the leads 20. Surgery is required to replace the batteries of the neurostimulator 40 every three to six years, depending on use.

The leads 20 represent the least reliable part of the system shown in FIG. 1. Lead fracture is reported to be the most frequent failure of the system which typically necessitates a major surgery to correct the problem and replace the leads 20. There have been reported attempts to eliminate implant's leads, a major source of complications and reliability issue. There have been reported attempts to deal with the complications and limitations imposed by the use of electrical leads. For example, self-contained implantable microstimulators and remotely-powered microstimulators have been described; however, each approach suffers from some significant limitation. A self-contained microstimulator must incorporate a battery or some other power supply; this imposes constraints on size, device lifetime, available stimulation energy, or all three. Often, DBS devices contain rechargeable batteries due to high use or high energy requirements of the therapeutic stimulation. Implantation of the pulse generator into the skull has been proposed, which addresses the difficult procedural task of tunneling leads and avoids cosmetic appearance issues associated with the subcutaneous leads and pulse generators; however, the lead still must be placed into the brain and connected to the pulse generator.

As for remotely-powered devices, designs utilizing either radiofrequency (RF) or electromagnetic transformer power transmission have been proposed in the prior art. RF energy transmission, unless the transmitting and receiving antennae are placed in close proximity, suffers from inefficiency and restricted safe power transfer capabilities, limiting its usefulness in applications where stimulation must be accomplished at any significant depth (>1-2 cm) within the body, in particular where it is desired to permanently implant both the transmitter and receiver-stimulator. Electromagnetic coupling can more efficiently transfer electrical power, and can safely transfer higher levels of energy but again relies on close proximity between transmitting and receiving coils, or the utilization of relatively large devices for deeper implantation.

The following patents, all of which are incorporated in this disclosure in their entirety, describe various aspects of using electrical stimulation for achieving various beneficial effects. U.S. Pat. No. 5,716,377 titled "Method of Treating Movement Disorders by Brain Stimulation" by Rise et al. describes a typical implantable DBS system for treating movement disorders such as Parkinson's. U.S. Pat. No. 7,013,177 titled "Treatment of Pain by Brain Stimulation" by Whitehurst et al. describes an implantable DBS system that uses electrical stimulation in the form of a microstimulator in combination with drug delivery for the treatment of pain. U.S. Pat. No. 5,405,367 titled "Structure and Method of Manufacture of an Implantable Microstimulator" by Schulman et al. describes an implantable microstimulator used generally for stimulation of tissue. U.S. Pat. No. 6,037,704 titled "Ultrasonic Power Communication System" by Welle describes the use of ultrasound energy transfer from a transmitter to a receiver for purposes of powering a sensor or actuator without being connected by a lead/wire. U.S. Pat. No. 6,366,816 titled "Electronic Stimulation Equipment with Wireless Satellite Units" by Marchesi describes a tissue stimulation system based on a wireless radio transmission requiring the charging of a battery at the receiver and separate command signals used to control the delivery of stimulation. German patent application DE4330680A1 titled "Device for Electrical Stimulation of Cells within a Living Human or Animal" by Zwicker describes a general approach to power transfer using acoustic energy for tissue stimulation. U.S. Pat. No. 7,010,351 titled "Methods and apparatus for effectuating a lasting change in a neural-function of a patient" by Firlik et al. describes a DBS system used to treat or effectuate changes to neural function particularly by stimulation in the region of the cortex. U.S. Pat. No. 6,427,086 titled "Means and method for the intracranial placement of a neurostimulator" by Fischell et al. describes a DBS device implanted in the skull. U.S. Pat. No. 6,016,449 titled "System for treatment of neurological disorders" by Fischell et al. describes the use of a DBS device for the treatment of epilepsy. U.S. Pat. No. 5,782,798 titled "Techniques for treating eating disorders by brain stimulation and drug infusion" by Rise describes a DBS system for treating eating disorders with electrical stimulation in regions of the brain.

Figure 2:
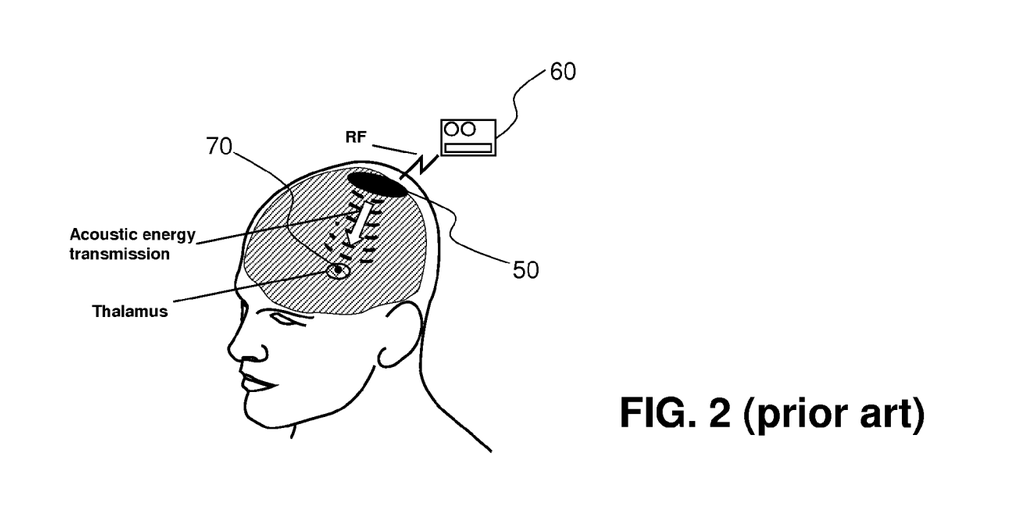
FIG. 2 is an example of the prior art showing a leadless ultrasound DBS system with unfocused transmission of acoustic energy.

There are known attempts to use ultrasound for leadless stimulation but the efficiency of acoustic delivery of energy to the electrodes appeared to be very low. FIG. 2 illustrates an idea of DBS proposed in the U.S. Pat. No. 7,894,904 by Cowan et al. (incorporated herein by reference in its entirety), where a brain stimulation capability is achieved without the use of leads connected to a stimulation controller/pulse generator. Plane unfocused acoustic waves are used to deliver acoustic energy from the implanted in the skull controller-transmitter device 50 to the actual stimulator 70 implanted in the target area in the brain. An external controller 60 is used to communicate with the internal controller 50 via RF signal transmission for making adjustments to its operation. The proposed system of ultrasonic leadless delivery of energy to the stimulator may provide the complete control of the electrical pulse parameters; that is, the pulse amplitude, pulse duration, frequency, and the number of pulses. However, estimates show that only a tiny fraction, less than 0.1%, of acoustic energy is delivered to the stimulator. In such arrangement it is difficult to deliver sufficient levels of acoustic energy to the stimulator without negatively affecting (overheating) surrounding tissues.

Poor energy efficiency of currently known systems is a major obstacle to broad use of leadless implantable device. The need exists therefore for a system capable of delivering sufficient energy to the implantable stimulator without excessive heating of surrounding tissues.

Better focusing of ultrasound on the location of the stimulator may help to solve this problem. Focusing of ultrasonic waves is a fundamental feature of most medical applications of ultrasound. The efficiency of conventional methods of ultrasound focusing is often limited in biological tissues by spatial heterogeneities in sound velocity and by reflective surfaces and boundaries. This challenge is especially great for focusing through the skull bone, which induces severe refractions and scattering of the ultrasonic beam. There are many methods of improving ultrasonic focusing in complex media based on phase and amplitude corrections in the focusing system, but they are often complicated, and, in some cases, do not provide the necessary improvement.

An effective method for focusing in heterogeneous medium is a concept of Time-Reversed Acoustics (TRA), which provides an elegant possibility of both temporal and spatial concentrating of acoustic energy. It was initially developed by M. Fink of the University of Paris. The TRA technique is based on the reciprocity of acoustic propagation, which implies that the time-reversed version of an incident pressure field naturally refocuses on its source. The general concept of TRA is described in a seminal article by Fink, entitled "Time-reversed acoustics," Scientific American, November 1999, pp. 91-97, which is incorporated herein by reference. U.S. Pat. No. 5,092,336 to Fink, which is also incorporated herein by reference, describes a device for localization and focusing of acoustic waves in tissues.

An important issue in the TRA method of focusing acoustic energy is related to obtaining initial signal from the target area. It is necessary to have a beacon located at the desired tissue location to record and provide an initial signal from the focal region. In the TRA systems described in the prior art, most commonly used beacon is a hydrophone placed at the chosen target point. Other disclosed beacons may include highly reflective targets that provide an acoustical feedback signal for TRA focusing of acoustic beam. The need to have a beacon in the target region limits the applications of TRA focusing methods.

While scattering and numerous reflections from boundaries are known to greatly limit and even completely diminish conventional ultrasound focusing, in TRA they lead to the improvement of the focusing results. Fink et al. have demonstrated a remarkable robustness of TRA focusing: the more complex the medium, the sharper the focus.

There is a need therefore for a leadless deep brain stimulation system configured for focused energy transmission to a specific site of the stimulator placement.

SUMMARY OF THE INVENTION

Accordingly, it is an object of the present invention to overcome these and other drawbacks of the prior art by providing a novel leadless neurostimulation system capable of focused energy delivery at the desired part of the brain.

It is another object of the present invention to provide a system that includes both implantable and external elements collaborating together in transmitting the required energy and control signals to the desired stimulation site in the brain.

It is a further object of the present invention to provide a system for focused delivery of ultrasound energy based on principles of time-reversal acoustics and using a skull as a reverberation chamber.

The leadless deep brain stimulation system of the invention includes an implantable stimulator configured to convert incoming acoustic energy into an electric stimulation signal appropriate for its intended therapeutic purpose. The acoustic energy is provided by one or more external transmitters located in close contact with the skin of the subject's head so as to be acoustically coupled thereto. To focus the transmission of ultrasound energy onto the location of the implanted stimulator, a wireless beacon (including a piezoelectric receiving transducer and an RF emitting antenna) is incorporated with the stimulator for providing an electromagnetic feedback signal to the time-reversal portion of the external controller.

The external controller is in turn configured to send an initial unfocused acoustic signal towards the stimulator. The stimulator then receives the acoustic waveform after reverberation in the skull and generates a radiofrequency feedback signal. That signal is subsequently received by the RF antenna of the external assembly and sent to the TRA controller. The signal is then time-reversed and used to send a second acoustic signal towards the stimulator. This acoustic signal is inherently focused on the site of the stimulator and is configured to carry sufficient energy to operate the stimulator for DBS purposes. Focusing of acoustic energy may be repeated from time to time to assure proper energy delivery only to the site of the stimulator and not to surrounding tissues.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE PREFERRED EMBODIMENT OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The leadless DBS system of the present invention is advantageously configured to focus ultrasound energy from an external source on an implantable miniaturized stimulator for the purpose of providing energy to the stimulator and to cause the stimulator to generate desired therapeutic electrical stimulation of the target brain tissue.

Figure 3A:
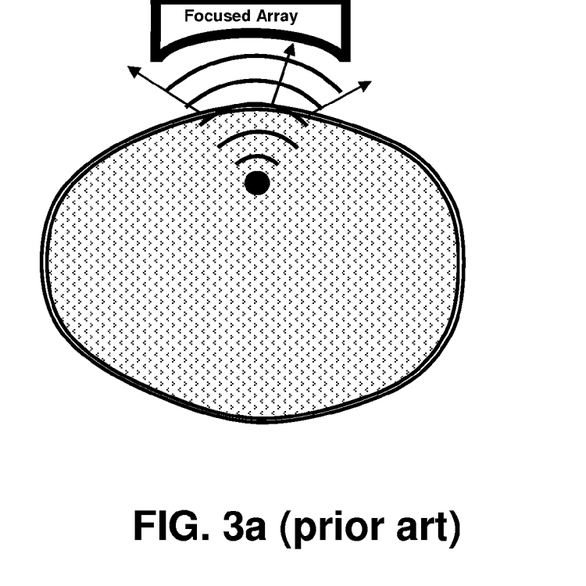
FIG. 3a shows a concept of conventional focusing of ultrasound signal in the brain.
Figure 3B:
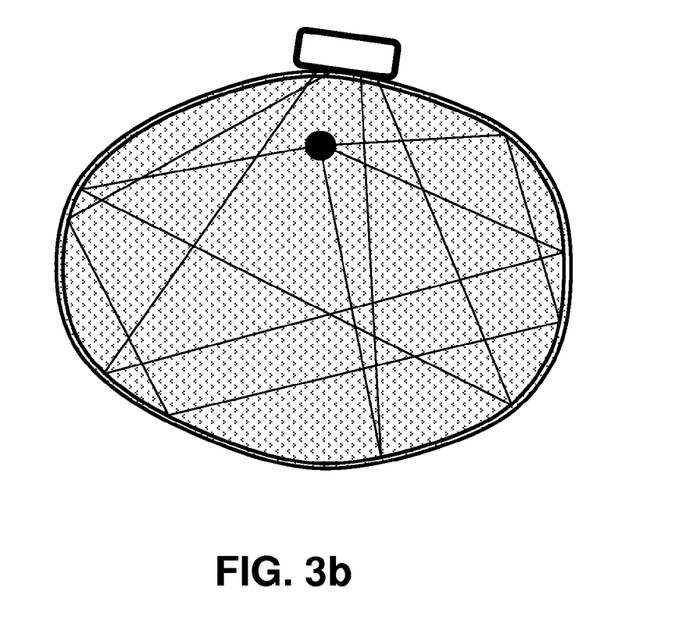
FIG. 3b shows TRA focusing of ultrasound signal in the brain according to the present invention.

FIGS. 3a and 3b are used to highlight the difference between conventional and TRA focusing of ultrasound waves inside the brain. FIG. 3a shows a conventional image-guided ultrasound focusing system, such as for example using a phased array plurality of transducers. In case of focusing the ultrasound signal inside the brain, this system suffers from multiple reflections off the internal surface area of the skull and may require complex phase corrections to compensate for it.

As compared with a phased array, the TRA focusing of ultrasound does not require image-based spatial guidance and may actually benefit from multiple reflections of the ultrasound waveform inside the skull—see FIG. 3b. TRA focusing process may be presented as a two-stage process. The first stage includes multiple reflections and random scattering of initial unfocused acoustical wave signal in a skull acting as a reverberator chamber. As a result, a continuous pattern of the ultrasound signal amplitudes and phases is formed on the reverberator's radiating surface which in this case is an internal surface of the skull. The complex signal is then received at the intended target area and time-reversed. In the second stage of the process, the time-reversed signal is emitted at the same initial point. The internal surface area of the skull acts as a virtual phased array to focus ultrasound on the target region. TRA may be very efficient for focusing on a target in the brain because the skull acting as a reverberator with a complex shape of its internal surface area helping ultimately to concentrate acoustic energy and direct it to the target.

In contrast to conventional ultrasound focusing techniques, TRA focusing additionally allows concentration of acoustic energy not only in space but also in time. That is, the duration of the high intensity ultrasonic pulse in the focal point of the TRA device can be several orders of magnitude shorter than the transmitted signal. Such temporal compression of ultrasound signal makes it possible to use lower power ultrasonic systems than conventional systems used for high intensity ultrasound therapy.

Together with its intrinsic advantage, one limitation of TRA focusing is that it relies on obtaining an initial feedback signal from the target area. Typically, a transducer (a hydrophone) needs to be placed in the target region to get necessary feedback acoustic signal for establishing the TRA relationship between the transmitter and the target site.

To overcome this limitation, the leadless DBS system of the present invention is configured to utilize electromagnetic radiofrequency (RF) signal as feedback. This approach makes use of the fact that a piezotransducer sonicated by an ultrasonic pulse (with a central frequency at or close to the resonance frequency of the piezotransducer) generates an RF electrical signal corresponding to the waveform of the ultrasonic pulse. A miniature piezotransducer may be incorporated in the implanted stimulator and configured to generate an RF signal in response to the received initial unfocused ultrasonic pulse. This signal may be emitted by an embedded RF antenna and used as a feedback signal for an accurate focusing of ultrasonic energy at the location of the implant using TRA focusing technique. Implementation of this approach may greatly simplify many aspects of the leadless DBS system.

Figure 4:
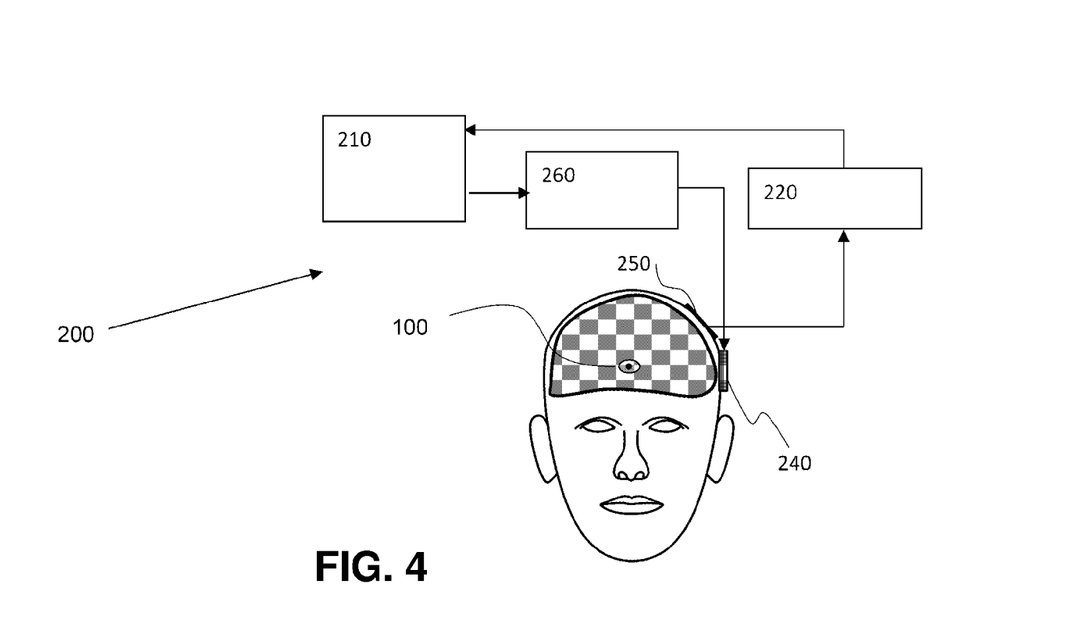
FIG. 4 is a block-diagram of the system of the invention.

FIG. 4 shows a schematic diagram of the leadless DBS system of the invention. It shows a first implantable stimulator 100 placed at the first desired part of the brain and an external assembly of the TRA system 200 configured for transmission of acoustic energy to at least the first stimulator 100. The stimulator 100 contains an electrically-activated internal neurostimulator electrical circuit capable of generating electrical stimulation signals and patterns suitable for a particular therapeutic purpose of the DBS system.

Figure 5:
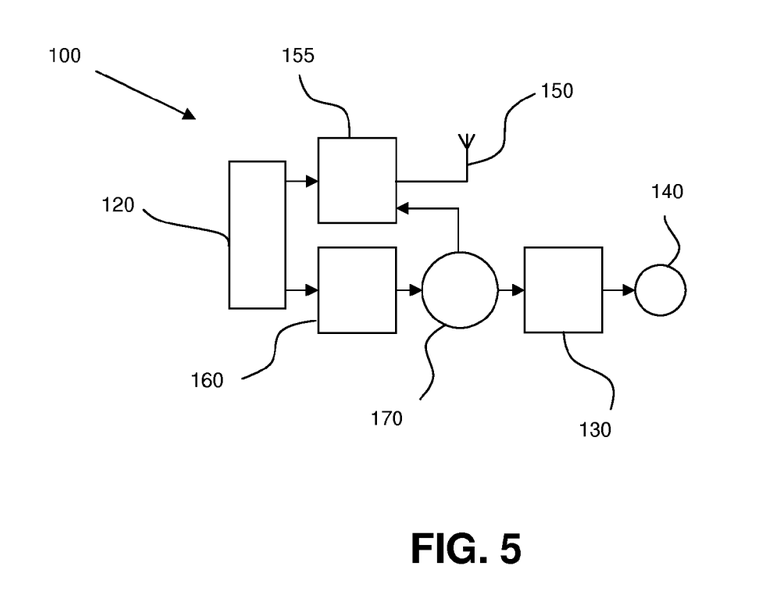
FIG. 5 is a block-diagram of the implantable stimulator of the invention.

The first stimulator 100 is shown in greater detail in FIG. 5 and includes a first piezoelectric receiving transducer 120, which serves for two purposes: (i) it receives the initial unfocused signal and generates a radiofrequency feedback signal, and (ii) it converts transmitted focused acoustic energy into an electrical power for the operation of the internal neurostimulator electrical circuit 130, the input of which is operably coupled with the electrical output of the receiving piezoelectric transducer 120. The internal electrical circuit 130 may include a charger 160 for a battery 170 and/or a signal conditioner which may have one of many known circuit configurations, producing an appropriate voltage pulse for brain stimulation. Importantly, the battery 170 may be selected to be dramatically smaller as compared with the internal batteries of conventional neurostimulators because it may be frequently recharged using the acoustic energy as described herein. Conventional neurostimulators on the other hand have to incorporate a battery with a sufficient charge required for several years of operation—dictating a battery choice with much larger volume and weight.

The electrical signal from the internal electrical circuit 130 may be applied then to one or more brain stimulating electrodes 140 operably coupled to the output of the internal electrical circuit 130. Such electrodes may be incorporated onto the outer surface of the housing of the stimulator 100, and thus be in direct contact with the brain tissue which is to be stimulated. Alternatively, the electrodes 140 may be placed at locations that are different from the location of the stimulator 100.

Electrical stimulation settings for electrodes 140 may be adjusted for example by means of an embedded or remote programmer or by acoustically transmitting a new set of desired settings from an external assembly. The following stimulation parameters may be set and adjusted as the DBS therapy is progressing: frequency of electrical signal (0-400 Hz), pulse width (20-700 ms), voltage (0-15 V), and mode/duration of stimulation including continuous, intermittent, or on-demand. Several programming sessions may be necessary to optimize the system settings for a particular subject depending on the response from the subject.

In embodiments, the implantable stimulator 100 may further include an emitting antenna 150 operably coupled with the receiving piezoelectric transducer 120 via an RF amplifier 155 and configured to amplify the electromagnetic radiofrequency feedback signal before emitting it by the antenna 150. In other embodiments, the piezoelectric receiving transducer 120 may be configured to emit the radiofrequency feedback signal directly, without the antenna of additional electric circuitry.

The first piezoelectric receiving transducer 120 and other components of the first implantable stimulator 100 may be enclosed within a hermetically sealed housing made of a biologically compatible material such as for example stainless steel or titanium. Such housing may be constructed to be electrically insulating but acoustically transparent. Its circuit assembly may be fabricated using known surface-mount or hybrid assembly techniques, upon either a fiberglass or ceramic substrate. Stimulating electrodes may be fabricated of materials commonly used in implanted electrodes, such as platinum or platinum-iridium design. Necessary electrical functional connections between the receiving transducer 120, internal electrical circuit 130, and electrodes 140 are shown in the drawings. The stimulator 100 of this design may also incorporate means such as helical coils, barbs, tines, clips, and the like (not shown) to affix the device within, or attach or wrap it onto, or place it in direct contact with the brain tissue at the desired location. Such fixation elements may vary depending on the intended implant location and delivery method. Typical dimensions of the stimulator 100 may be 1.5 cm in length by 3 mm in diameter, and preferably less than 1.0 cm in length by 2 mm in diameter, exclusive of fixation elements.

Utilizing current surgical techniques to access regions of the brain, the first miniaturized stimulator 100 may be implanted into a first target brain tissue or attached to the desired location in contact with the first target brain tissue. Various techniques and tools for cranial access and probing of brain tissue have been described which may be adapted to facilitate delivery of the stimulator 100 to these locations.

Once in place, the stimulator 100 may incorporate means to provide permanent attachment to the implant site as described above.

In embodiments, more than one implantable stimulators positioned at multiple target areas in the brain are envisioned. In one embodiment, a second implantable stimulator may be positioned at a second target are for brain stimulation. The second implantable stimulator may include a second piezoelectric receiving transducer, a second internal neurostimulator electrical circuit, a second emitting antenna and at least one second stimulator electrode placed in electrical contact with the second target area in the subject's head. In other embodiments, more than two implantable stimulators are envisioned to provide desired DBS therapy at more than two target areas in the brain.

To operate multiple implantable stimulators, there is a need to individually focus and then transmit acoustic wave signals on each of these implantable stimulators. The present invention provides for a unique ability of using one or more external transmitters to individually operate several implantable stimulators. This is accomplished by using different central frequencies for emitting acoustic wave signals, each of the central frequencies may be matched to a resonant frequency of a corresponding piezoelectric receiving transducer in each corresponding implantable stimulator. Emitting an initial unfocused acoustic wave signal followed by a focused acoustic wave signal using a specific frequency band with a central frequency corresponding to the resonant frequency of the intended piezoelectric receiving transducer allows the DBS system of the present invention to selectively address and energize individual implantable stimulators as required. To exclude "cross-talk" between more than one implantable stimulator, the difference between a first central frequency and a second (or more) central frequency may be at least 20%. This difference effectively eliminates an overlap between frequency bands for operating the first and the second implantable stimulator.

Referring back to the general schematic of the leadless DBS system of the invention shown FIG. 4, the external assembly of the system may include the following:
- a battery-operated TRA controller 210 configured to receive, time-reverse, and amplify the electromagnetic radiofrequency feedback signal; the TRA controller 210 may also include a control and timing module, which stores setup parameters and uses this information in conjunction with the acquired TRA feedback signal to generate the required initial and driving signals for the ultrasound amplifier 260, which in turn operates the ultrasound emitting transducer 240,
- an emitting acoustic transducer 240 to produce the desired initial unfocused and then focused acoustic wave signal, and
- an RF receiver 220 operably coupled to a receiving RF antenna 250, all assembled on or within an appropriate housing as described later. The external assembly elements may be located at one or more locations around the head such that one or more ultrasound emitting transducers 240 may be placed in close contact (to be acoustically coupled) with the skin of the subject at a location on the head suitable for transmission of ultrasound energy towards the location of the implantable stimulator 100 such as a temporal bone. To assure acoustic coupling with the skull of the subject, an acoustic coupling media may be added to the external surface of the emitting transducer 240, such as an acoustic coupling gel, fluid, lubricant or other known media. The subject may also be asked to prepare the skin for the best possible acoustic contact such as to closely shave all hair and so on.

An important consideration for proper operation of the DBS system of the invention is selection of the bandwidth and central operating frequency for the emitting transducer 240. The bandwidth and the central frequency may be selected to be the same or close to that of the receiving piezoelectric transducer 120. The bandwidth and the central frequency for the initial unfocused acoustic signal and for the subsequently time-reversed focused acoustic wave signal may correspond to that of the emitting acoustic transducer 240. The bandwidth may depend on the duration of the acoustic wave signals and may be wider for shorter signals and narrower for longer signals.

As to the central frequency guidance, ideally the geometrical focusing area of the ultrasound energy should be concentrated only on the piezoelectric receiving transducer 120 and not on surrounding tissues. Assuming the length of the piezotransducer to be several millimeters (5 mm as an this example), the central operating frequency of the emitting acoustic transducer 240 may be selected to be about 150 kHz making the focusing area sized to be about half of the wavelength to correspond to the size of the piezotransducer. Increasing the operating frequency may be done up to about 500 kHz above which the ability of the skull to act as an effective reverberator to properly reflect the ultrasound signal multiple times without losing the signal strength may be compromised. Lowering the operating frequency will increase the dimensions of the acoustic focal spot and eventually eliminate the advantage of the TRA focusing of acoustic energy. An operating frequency selected to be lower than about 30 kHz will produce a focal spot with dimensions in the range of a few centimeters which is much larger than the area occupied by the implanted neurostimulator and as a result, ultrasound may significantly affect the surrounding brain tissues. Therefore, the desired central operating frequency for the ultrasound emitting transducer may be selected in a range of about 30 kHz to 500 kHz and preferably close to about 150 kHz.

In case of multiple implantable stimulators, the DBS system may include one or more broadband emitting transducers capable of emitting an acoustic wave signal at the above described frequency range of 30 kHz to 500 kHz while individual central operating frequencies for each implantable stimulator may be selected to differ by at least 20% while all in the same general frequency range. Such arrangement will allow external emitting transducer to focus and operate each of the implantable stimulators individually.

Figure 6:
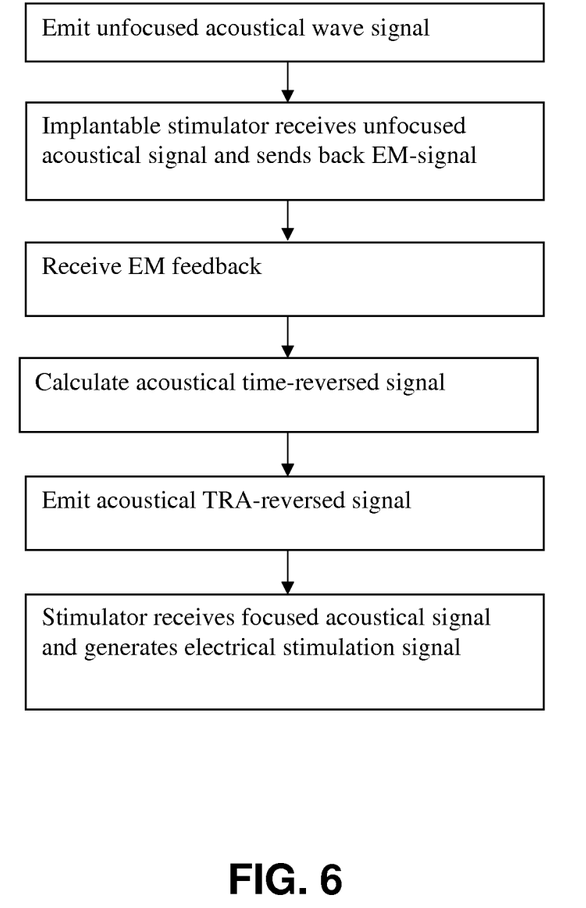
FIG. 6 is a flowchart of the major steps involved in operation of the leadless DBS system of the invention.

Once the leadless DBS system is positioned around the head of the subject and is able to communicate with the implantable stimulator 100 by sending ultrasound signals towards it and receiving EM radiofrequency feedback signal therefrom, the operation of the DBS system of the invention may proceed in the following manner shown schematically in FIG. 6:
- a. emission of the initial unfocused acoustic pulse or a burst signal;
- b. receiving of the ultrasound signal by the piezoelectric transducer 120 of the stimulator 100 after reverberation in the skull, followed by generating and emitting of the received waveform as an electromagnetic feedback signal by the RF emitting antenna 150;
- c. receiving of the EM feedback signal by the RF receiving antenna 250, processing and transmission to the TRA controller 210;
- d. calculating of the acoustical time-reversed signal by the TRA controller 210 e. emitting of the acoustic TRA-reversed signal by the emitting acoustic transducer 240, such signal is formed by the TRA controller 210 using the time-reversed signal from previous steps and amplified by the power amplifier 260;

f. the focused acoustic wave signal is received by the stimulator 100, converted to electrical power and is used to generate therapeutic electrical signals for DBS purposes.

Once the initial focusing on the location of the implantable stimulator 100 is achieved, one or more re-focusing procedures may be implemented by the leadless DBS system of the invention. Although it is unlikely that the implantable stimulator 100 may be moved from its original location, it is still possible to see some minor location shifts due to blood flow, tissue swelling or other factors. It is also likely that the external emitting transducer 240 may be shifted from its original position. Re-focusing may be done the same way as the initial focusing. Such re-focusing may be triggered manually from time to time, or may be based on a detected loss of energy transmitted to the implantable stimulator 100, or may be done on a routine schedule, such as every 5 sec, 20 sec, 1 min, or 10 min of operation.

As mentioned above, one advantageous location for the emitting acoustic transducer 240 may be over a temporal bone of the skull. Close positioning of the transducer at this location may provide the desired acoustic coupling between the emitting transducer 240 and the head of the subject, especially when an acoustic coupling media is used. This location is also convenient for incorporating the emitting transducer into a "smart hat" 80 which in turn may also be used to house other elements of the external assembly of the DBS system—see FIG. 7. The smart hat may include an elastic band to assure close positioning and retention of the emitting transducers next to the head of the subject.

Figure 7:
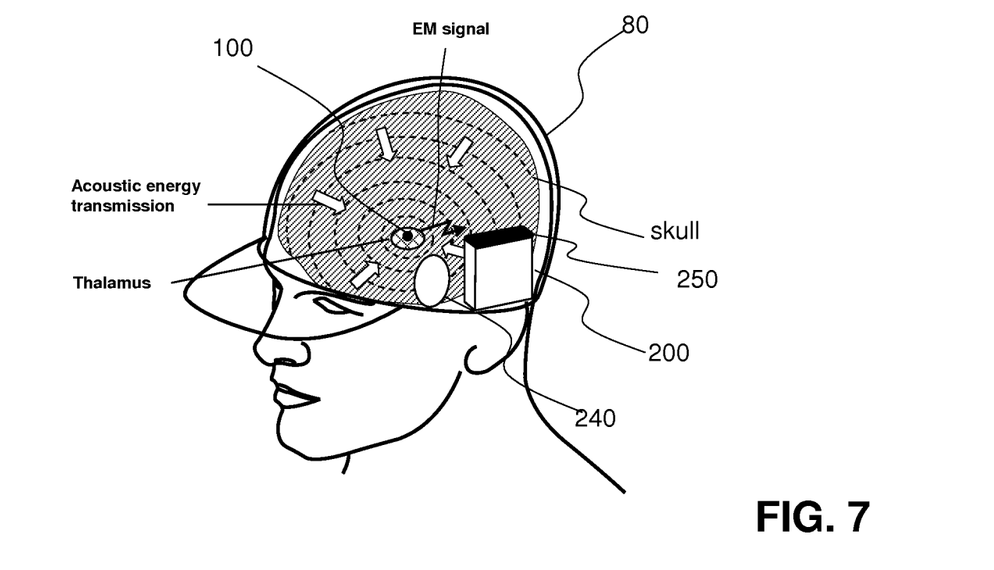
FIG. 7 shows a first embodiment of the invention in which a "smart hat" is used to house the external elements of the leadless DBS system.
Figure 8:
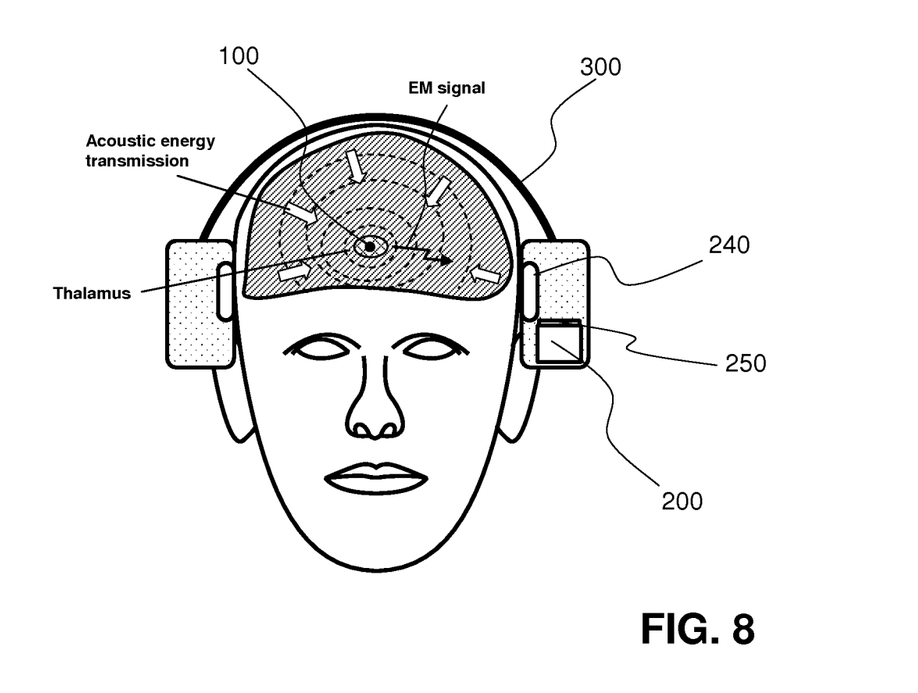
FIG. 8 shows a second embodiment of the invention in which elements of the leadless DBS system are retained next to the skull of the subject using headphones-style U-shaped elastic holder.
Figure 9:
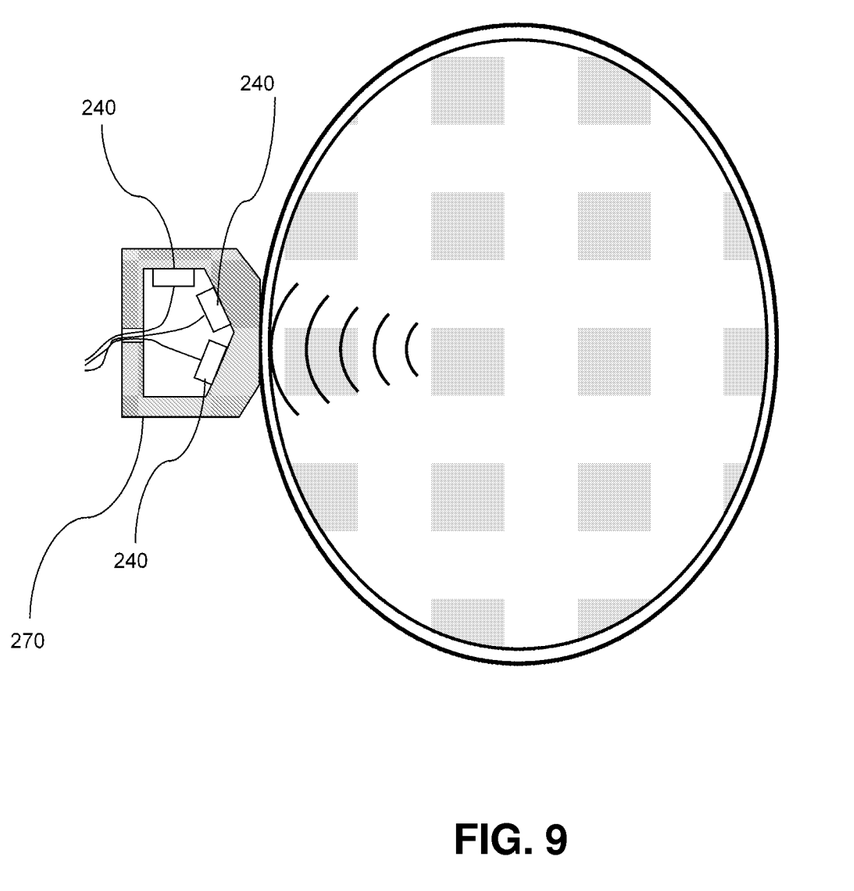
FIG. 9 shows a transmitter including an external reverberator with a plurality of individual emitting acoustic transducers.

In embodiments, one or more emitting ultrasound transducers may be included in the smart hat 80. In one embodiment, there is only one such emitting acoustic transducer as shown in FIG. 7. In another embodiment, such as that shown in FIG. 8, there is present a left emitting acoustic transducer and a right emitting acoustic transducer. In other embodiments, as shown in FIG. 9, several emitting transducers may be included in an external reverberator 270. A plurality of individual emitting acoustic transducers 240 may be attached and operatively coupled to the internal chambers of the external reverberator, for example by gluing to the internal surfaces of the reverberator. The details of such arrangements were described in my previous patent applications cited above.

The system may further include more than one external reverberators of a similar design. Using one or more external reverberators may cause the acoustic signal from the emitting transducer to travel and reflect throughout the external reverberator as well as throughout the skull of the subject before reaching the implantable stimulator, therefore providing for a stronger focusing opportunity for the DBS system of the present invention. Using this arrangement necessitates the external reverberators to be acoustically coupled to the temporal bones of the subject, such as by using a coupling gel or lubricant.

A system including multiple emitting acoustic transducers 240 and at least one external reverberator 270 incorporated into a smart hat 80 may be operated by first individually tuning each of the emitting acoustic transducers 240 to emit an individual focused acoustic wave signal. Such tuning may be accomplished by activating each emitting transducer 240 one-at-a-time to first emit an initial unfocused signal. These unfocused signals may be then received one-at-a-time by the piezoelectric receiving transducer 120 of the implantable stimulator 100, individually converted into a radiofrequency feedback signal and emitted by the RF antenna 150. These individual feedback signals may then be received by the external assembly of the system, individually time-reversed and stored in memory. To generate the focused acoustic wave signal, all of the individual emitting transducers 240 may be activated synchronously using their respective individual time-reversed signals. Synchronous operation allows maximizing and concentrating energy delivery using a plurality of individual emitting transducers 240. Importantly, such synchronization may take into account different lengths of time for each individual emitted acoustic wave signal to reach the piezoelectric receiving transducer 120. If such difference in travel time is detected, activation of individual emitting transducers 240 may be appropriately staged such that to assure that all acoustic wave signals reach their target at the same time.

Other suitable means to retain the elements of the leadless DBS system around the head of the subject are also contemplated in the present invention. FIG. 8 shows a headphones-style arrangement in which a U-shaped elastic holder 300 may be configured to retain either one, two (left and right), or more emitting transducers 240 next to the left, right or both temporal bones of the skull and configured to send ultrasound signals towards the implantable stimulator 100. The system also supports the TRA controller 200 with incorporated RF receiving antenna 250. As with the smart hat embodiment, a plurality of emitting transducers may be included and operated in a similar manner.

The delivery of ultrasound energy and, therefore, electrical stimulation could either be automatically triggered based on information received from an internal or external physiological sensor, or be based upon programmed settings, or be manually activated by the subject, physician or other individuals. More specifically, the timing of the initiation of the delivery and/or the duration of the delivery and/or the energy content of the delivery and/or the information content of the delivery may be based upon sensor information or based upon programmed settings or be manually controlled.

To operate the leadless DBS system of the present invention, an appropriate user interface may be provided. In embodiments, such user interface may include a simple button to initiate and stop the preprogrammed operation of the system. In other embodiments, a more sophisticated user interface may allow to adjust the stimulation parameters in the ranges as described above as well as to activate the system for continuous, intermittent or on-demand modes of operation.

The elements of the user interface may be incorporated into the external assembly and be accessible for example on the exterior surface of the smart hat or the U-shaped holder as described above. In other embodiments, some or all elements and buttons of the user interface may be incorporated into a wireless controller, which may be configured to communicate with the external assembly and/or the implantable stimulator using one of the well known methods of wireless communication such as Bluetooth or others. The wireless controller may also include a display to communicate the status of the DSB system before, during, or after its operation.

The principles described above for designing and operating a leadless DBS system may be applicable to either configure the system de-novo as described above or to provide power to an existing neurostimulator. In this case, the subsystem of the invention may be used to energize a existing device, which prior to that could have been operated using battery energy. This approach will obviate the need to conduct a stimulator replacement surgery when the battery runs out.

The herein described subject matter sometimes illustrates different components or elements contained within, or connected with, different other components or elements. It is to be understood that such depicted architectures are merely examples, and that in fact many other architectures may be implemented which achieve the same functionality.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A leadless system for deep brain stimulation of a subject based on time-reversal acoustics, the system comprising:
 a first implantable stimulator in a hermetically sealed housing, said stimulator in turn comprising:
  a first piezoelectric receiving transducer,
  an emitting antenna configured for emitting a radiofrequency feedback signal, said emitting antenna is operably coupled to said piezoelectric receiving transducer,
  an internal electrical circuit with an input operably coupled to said piezoelectric receiving transducer, said internal electrical circuit configured to be powered by said piezoelectric receiving transducer and to generate an electrical stimulation signal for deep brain stimulation, and
  a first stimulating electrode operably coupled to an output of said internal electrical circuit, said first stimulating electrode configured to be in electrical contact with a first target brain portion of said subject, and
 an external assembly comprising:
  a time-reversal controller,
  a radiofrequency receiving antenna,
  a radiofrequency signal receiver with an input operably coupled with said radiofrequency receiving antenna and an output operably coupled with an input of said time-reversal controller,
  an emitting acoustic transducer with an input operably coupled to an output of said time-reversal electronic unit,
 wherein said external assembly is configured to emit a first initial unfocused acoustic wave signal, said first piezoelectric receiving transducer is configured to receive said first unfocused acoustic wave signal after reverberation in a skull of the subject and generate an electromagnetic radiofrequency feedback signal, said external assembly is further configured to receive said radiofrequency feedback signal, time-reverse thereof and generate a first driving signal to cause said emitting acoustic transducer to send a first acoustic wave signal focused on said first piezoelectric receiving transducer to generate electrical energy sufficient to operate said first implantable stimulator for the purpose of deep brain stimulation.

2. The system as in claim 1, wherein said first unfocused wave signal and said first focused acoustic wave signal are emitted at a first central frequency in a range from 30 kHz to 500 kHz.

3. The system as in claim 1 further comprising a second implantable stimulator having a second piezoelectric receiving transducer and a second stimulating electrode configured to be placed in electrical contact with a second target brain portion of said subject.

4. The system as in claim 3, wherein said external assembly is configured to generate said first unfocused acoustic wave signal and said first focused acoustic wave signal at said first central frequency corresponding to a resonance frequency of said first piezoelectric receiving transducer,
 said external assembly is further configured to generate a second unfocused acoustic wave signal, time-reverse a second received radiofrequency feedback and generate a second focused acoustic wave signal at a second central frequency corresponding to a resonance frequency of said second piezoelectric receiving transducer,
 whereby said external assembly is configured for selective deep brain stimulation at more than one target brain portion of the subject.

5. The system as in claim 4, wherein one of said first central frequency or said second central frequency is selected to exceed the other by at least 20% while both of said first and second central frequencies are selected in a range from 30 kHz to 500 kHz.

6. The system as in claim 1 further comprising an acoustic coupling media on said emitting acoustic transducer.

7. The system as in claim 1, wherein said external assembly further comprises a plurality of individual emitting acoustic transducers.

8. The system as in claim 7, wherein said external assembly further comprising an external reverberator, whereby said first initial unfocused acoustic wave is reaching said first piezoelectric receiving transducer after reverberation in both said external reverberator and said skull of said subject.

9. The system as in claim 8, wherein at least some of said plurality of individual acoustic transducers are attached and operatively coupled to said external reverberator.

10. The system as in claim 7, wherein said time-reversal controller is configured to activate said individual acoustic transducers to generate initial unfocused acoustic wave signals one-at-a-time, said time-reversal controller is further configured to receive respective radiofrequency feedback signals one-at-a-time and generate respective individual time-reversed driving signals for each individual emitting acoustic transducer, said time-reversal controller is further configured to operate all of said individual emitting acoustic transducers synchronously to generate said focused acoustic wave signal and to energize said first implantable stimulator.

11. The system as in claim 9, wherein said external assembly comprises a left external reverberator and at least one left emitting transducer operatively coupled thereto, together said left external reverberator and said at least one left emitting transducer forming a left emitting transmitter, said external assembly further including a right external reverberator and at least one right emitting transducer operatively coupled thereto, together said right external reverberator and said at least one right emitting transducer forming a right emitting transmitter.

12. The system as in claim 11, wherein said left emitting transmitter and said right emitting transmitter are enclosed in a hat sized to be firmly placed over the head of the subject.

13. The system as in claim 12, wherein the position of said left emitting transmitter and said right emitting transmitter in said hat is selected to assure their respective placement adjacent to left and right temporal bones of the skull when the subject wears said hat.

14. The system as in claim 11, wherein said left emitting transmitter and said right emitting transmitter are attached to a U-shaped elastic holder, said holder is shaped and sized to be placed over the head of the subject and retain said emitting transmitters next to the respective temporal bones of the subject.

15. The system as in claim 1, wherein said external assembly further includes a user interface configured to provide manual control to start, stop, and adjust said deep brain stimulation.

16. The system as in claim 15, wherein said user interface is configured for activation of a deep brain stimulation session with preset parameters and for a preset duration, whereby said system is configured for "on demand" activation by the subject.

17. The system as in claim 15 further including a wireless controller configured for wireless communication with said external assembly, said wireless controller including at least a portion of said user interface.

18. The system as in claim 1, wherein said internal electrical circuit is configured to generate said electrical stimulation signal at a frequency from 0 to 400 Hz, at a pulse width from 20 to 700 ms, at a voltage from 0 to 15V and in a mode of operation selected from a group consisting of continuous stimulation, intermittent stimulation, and on-demand stimulation.

\* \* \* \* \*